(12) United States Patent
Arnebrant

(10) Patent No.: US 9,050,338 B2
(45) Date of Patent: Jun. 9, 2015

(54) MORPHOLINO COMPOUND MICROEMULSION

(75) Inventor: Thomas Arnebrant, Lomma (SE)

(73) Assignee: Sinclair Pharmaceuticals Limited, Chester (GB)

( * ) Notice: Subject to any disclaimer, the term of this patent is extended or adjusted under 35 U.S.C. 154(b) by 778 days.

(21) Appl. No.: 12/742,407

(22) PCT Filed: Dec. 19, 2007

(86) PCT No.: PCT/GB2007/004878
§ 371 (c)(1),
(2), (4) Date: Jul. 19, 2010

(87) PCT Pub. No.: WO2008/078076
PCT Pub. Date: Jul. 3, 2008

(65) Prior Publication Data
US 2010/0294686 A1    Nov. 25, 2010

(30) Foreign Application Priority Data
Dec. 22, 2006   (GB) .................................. 0625841.2

(51) Int. Cl.
| | |
|---|---|
| A61Q 11/00 | (2006.01) |
| A61K 8/49 | (2006.01) |
| A61K 31/5375 | (2006.01) |
| A61K 9/107 | (2006.01) |
| A61K 31/495 | (2006.01) |
| A61K 8/06 | (2006.01) |

(52) U.S. Cl.
CPC ............... *A61K 31/495* (2013.01); *A61K 8/068* (2013.01); *A61K 8/49* (2013.01); *A61Q 11/00* (2013.01); *A61K 9/1075* (2013.01)

(58) Field of Classification Search
None
See application file for complete search history.

(56) References Cited

U.S. PATENT DOCUMENTS

| | | | |
|---|---|---|---|
| 5,082,653 A | | 1/1992 | Pan et al. |
| 5,446,070 A | * | 8/1995 | Mantelle ..................... 514/772.6 |
| 5,853,740 A | * | 12/1998 | Lu et al. ......................... 424/400 |
| 2003/0082113 A1 | * | 5/2003 | Rajaiah et al. .................. 424/49 |
| 2005/0048005 A1 | * | 3/2005 | Stockel ........................... 424/49 |
| 2005/0192348 A1 | | 9/2005 | Bar-Or et al. |
| 2008/0299052 A1 | * | 12/2008 | Sjodin ............................ 424/53 |

OTHER PUBLICATIONS

Garti, N., Progress in Stabilization and Transport Phenomena of Double Emulsions in Food Applications, Lebensm.-Wiss. u.-Technol., 30, 222-235 (1997).*

J. C. Hase, R. Altstrom, S. Edwardsson, E. Kelty and J. Kisrch. 6-month use of 0.2% delmopinol hydrochloride in comparison with 0.2% chlorhexidine digluconate and placebo. Journal of clinical periodontology, vol. 25, Issue 9, pp. 746-753. Sep. 1993. (Abstract Only).*

Elworthy et al. "Antimicrobial properties of delmopinol against oral bacteria" *Letters in Applied Microbiology*, 1995, pp. 191-194, vol. 20, No. 3.

* cited by examiner

*Primary Examiner* — Brian Gulledge
*Assistant Examiner* — Michael P Cohen
(74) *Attorney, Agent, or Firm* — Saliwanchik, Lloyd & Eisenschenk

(57) ABSTRACT

An L2/L1 microemulsion composition comprising water, a compound of formula (I) wherein $R_1$ is a straight or branched alkyl group containing 8 to 16 carbon atoms at the 2- or 3-position of the morpholino ring, and $R_2$ is a straight or branched alkyl group containing 2 to 10 carbon atoms, substituted with a hydroxy group except in the alpha-position, and a salt of a compound of formula (I).

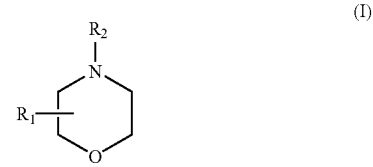

(I)

12 Claims, No Drawings

MORPHOLINO COMPOUND MICROEMULSION

CROSS REFERENCE TO A RELATED APPLICATION

This application is a National Stage Application of International Application Number PCT/GB2007/004878, filed Dec. 19, 2007; which claims priority to Great Britain Application No. 0625841.2, filed Dec. 22, 2006; which are incorporated herein by reference in their entirety.

FIELD OF THE INVENTION

The present invention relates to compositions comprising delmopinol or a derivative thereof.

BACKGROUND TO THE INVENTION

Delmopinol is a morpholino compound that has utility in the treatment of the oral cavity, in particular for the prevention and treatment of gingivitis and for the removal or inhibition of dental plaque. The compound and its manufacture are disclosed in U.S. Pat. No. 4,894,221.

Delmopinol Hydrochloride is used commonly in oral formulations, particularly mouth washes. However, delmopinol HCl is highly soluble in water and, when used in oral formulations, the delmopinol is removed from the oral surfaces (where it exerts its action) by the flow of saliva. Delmopinol HCl is so soluble that even in areas of the mouth with low saliva flow, it is only present for a relatively short time. Therefore, it is recommended that currently available products are held in the mouth for up to a minute, to achieve maximum efficacy. In addition, the concentration of delmopinol required for efficacy is high (0.2%) and contributes significantly to the cost of oral formulations.

There is a need for a formulation that provides delmopinol and related compounds in a form that will remain at oral surfaces for longer periods. Such a formulation will provide greater efficacy, at lower concentrations of delmopinol and/or when used for shorter periods of time, as a result of improved substantivity. In addition, the cost of the formulations should be reduced through achieving efficacy at a lower concentration of delmopinol.

SUMMARY OF THE INVENTION

The present invention is based on the surprising realisation that a microemulsion of an L2-phase in an L1-phase of a compound of formula I, a salt of a compound of formula I and water is, surprisingly, kinetically very stable and has improved substantivity.

According to a first aspect of the invention, an L2/L1 microemulsion composition comprises water, a compound of formula (I)

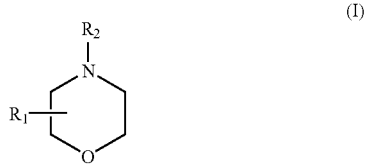

(I)

wherein $R_1$ is a straight or branched alkyl group containing 8 to 16 carbon atoms at the 2- or 3-position of the morpholino ring, and $R_2$ is a straight or branched alkyl group containing 2 to 10 carbon atoms, substituted with a hydroxy group except in the alpha-position, and a salt of a compound of formula (I).

According to a second aspect of the invention, a method of preparing an L2/L1 microemulsion composition comprising water, a compound of formula I and a salt of a compound of formula I, comprises the steps of:
(i) mixing 70-80% w/w formula (I) with 20-30% w/w of a salt of a compound of formula (I); and
(ii) adding water to the mixture formed by step (I), to at least 80% w/w, thereby forming an L2/L1 microemulsion.

According to a third aspect of the invention, a composition comprises a mixture of 70-80% w/w of a compound of formula (I) and 20-30% w/w of a salt of a compound of formula (I).

According to a fourth aspect of the invention, a composition according to the third aspect is used in the manufacture of a microemulsion.

According to a fifth aspect of the invention, a container comprises a composition according to the first or third aspects.

DETAILED DESCRIPTION OF THE INVENTION

The invention relates to compositions comprising a compound of formula I, a salt of a compound of formula I and water. It has been found, surprisingly, that water and a combination of a compound of formula I and a salt of a compound of formula I, when mixed to form an L2/L1 microemulsion, has improved in situ stability and substantivity.

As used herein, the term "substantivity" is to be given its usual meaning in the art, i.e. the amount of time that a substance remains associated with a surface. The term "substantivity" defines the length of time that a compound of formula (I) or a salt of a compound of formula I remains associated with a surface of the oral cavity such as the tongue, gums or preferably the teeth. The surface of the oral cavity may comprise additional agents, preferably bacteria or bacterial plaque. Substantivity may be measured using a desorption assay or ellipsometry. For example, substantivity may be measured by the desorbed amount released in solution (concentration assay) or by measuring the adsorbed mass at a surface using ellipsometry (a well-known technique based on measuring polarisation changes of light upon reflection). A microemulsion according to the present invention provides a composition with improved substantivity compared to conventional compositions. The skilled person will recognise that improved substantivity of a composition comprising a compound of formula I provides a more effective oral health composition.

The L2/L1 microemulsion comprising a compound of formula I, a salt of a compound of formula I and water, according to the present invention, also demonstrates improved stability compared to conventional compositions. The term "stability" refers to the kinetic stability of the composition and includes thermal stability. Stability can be detected by inspecting the droplet size distribution versus time, using optical microscopy.

The L2/L1 microemulsion of the invention comprises water, a morpholino compound of formula I and a salt of a compound of formula I. As used herein, the term "L2/L1 microemulsion" refers to an L2/L1 microemulsion containing droplets of less than or equal to 300 nm in diameter, preferably less than or equal to 200 nm in diameter and most preferably less than or equal to 100 nm in diameter, suspended in water. The "L2/L1" terminology is well known to one skilled in the art. An L2 emulsion is a water-in-oil emulsion and an L1 emulsion is an oil-in-water emulsion. Therefore, the L2/L1 microemulsion according to the present invention is a water-in-oil-in-water microemulsion.

As used herein, the term "emulsion" is to be given its normal meaning in the art, i.e. a dispersion in which one substance (the dispersed, or internal, phase) is dispersed in another (the continuous, or external, phase).

Determining the type of emulsion that is present in a composition is straightforward for one skilled in the art.

The L2/L1 microemulsion comprises a morpholino compound of formula (I). A morpholino compound according to the invention has the general formula (I)

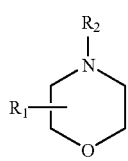
(I)

wherein $R_1$ is a straight or branched alkyl group containing 8 to 16 carbon atoms at the 2- or 3-position of the morpholino ring, and $R_2$ is a straight or branched alkyl group containing 2 to 10 carbon atoms, substituted with a hydroxy group except in the alpha-position, or pharmaceutically acceptable salts thereof. In a preferred embodiment, the sum of the carbon atoms in the groups $R_1$ and $R_2$ of the morpholino compound is at least 10, preferably between 10 and 20. In a further preferred embodiment, the $R_2$ group terminates with the hydroxy group.

The claimed morpholino compounds are known per se and can be manufactured by any known method, for example that disclosed in U.S. Pat. No. 5,082,653 and WO90/14342, which are incorporated herein by reference.

The preferred morpholino compound for use in the invention is 3-(4-propyl-heptyl)-4-(2-hydroxyethyl)morpholine, which is commonly known as Delmopinol (CAS No. 79874-76-3).

The composition of the invention also comprises a salt of a compound of formula (I). Any salt form can be used; preferably the salt is a pharmaceutically acceptable salt. Examples of pharmaceutically acceptable salts are the salts of acids such as acetic acid, phosphoric acid, boric acid, hydrochloric acid, maleic acid, benzoic acid, citric acid, malic acid, oxalic acid, tartaric acid, succinic acid, glutaric acid, gentisic acid, valeric acid, gallic acid, beta-resorcyclic acid, acetyl salicylic acid, salicylic acid, perchloric acid, barbituric acid, sulfanilic acid, phytic acid, p-nitro benzoic acid, stearic acid, palmitic acid, oleic acid, myristic acid, lauric acid and the like. The most preferred salts are those of hydrochloric acid. A preferred salt is delmopinol hydrochloride (CAS No. 98092-92-3).

For the avoidance of doubt, a compound of formula I is the "free base" form, i.e. a ternary amine which may be protonated below its pk. The preferred free base form is delmopinol. The microemulsion also comprises a salt form of a compound of formula I. Preferably the salt form is the hydrochloride salt. Preferably, the free base compound of formula I is present in the majority compared to the salt form. By the term "majority", it is meant that there is a larger amount of the free base compound of formula I than the salt form of a compound of formula I. More preferably, the (free base) compound of formula I is present at 70-80% w/w and the salt form is present at 20-30% w/w (such that the free base and salt form total 100% w/w of the compound present). The composition comprising a mixture of a compound of formula I and a salt form of a compound of formula I is itself a useful intermediate in the production of the microemulsion; this mixture can be made up and stored for subsequent use, if required.

The microemulsion comprises water. Preferably, the microemulsion comprises at least 50% w/w water, more preferably at least 80% w/w water, for example at least 85%, 90%, 95%, 98.8% or 99.8% w/w water. The microemulsion is most stable when it comprises greater than or equal to 80% w/w water.

For the avoidance of doubt, the microemulsion comprises water and a mixture of a compound a formula I and a salt of a compound of formula I. In the mixture of the compound and the salt, the compound of formula I is preferably present at 70-80% w/w and a salt of the compound of formula I is preferably present at 20-30% w/w. This mixture is combined with water to form a microemulsion. In the microemulsion, the water is present to at least 50% w/w. The remaining 50% w/w (or less) of the microemulsion comprises the mixture of the compound of formula I and a salt of a compound of formula I and, optionally, other agents (as detailed below).

In a preferred embodiment, the microemulsion comprises a small amount, i.e. less than 10% w/w, more preferably less than 5% w/w, for example 3% w/w or less, of glycerol. When glycerol is included, the amount of water is reduced by a corresponding amount, i.e. if 3% w/w glycerol is included, there will be 3% w/w less water (than if the glycerol was not present).

A preferred microemulsion composition comprises 90% w/w water, the balance comprising the mixture of a compound of formula I and the HCl salt of a compound of formula I. In one embodiment, the water, compound of formula I and the HCl salt of a compound of formula I are the only components in the composition, and therefore the water is present at 90% w/w and the mixture of a compound of formula I and a salt of a compound of formula I are present, together, at a total of 10% w/w. However, in an alternative embodiment, other agents are present. In a further embodiment, the compound of formula I, a salt of a compound of formula I and water are the only major, or active components present; the composition then consists essentially of these components.

In an alternative embodiment, a composition is prepared with less than or equal to 20% w/w water, preferably between 16% and 20% w/w water. The balance (e.g. 80% w/w or more, to total 100% w/w) comprises a mixture of a compound of formula I and a salt of a compound of formula I. This composition, containing 20% w/w or less water, is a useful intermediate that can subsequently be diluted with additional water, to the preferred level of at least 80% w/w, to provide a microemulsion composition (as described above) with improved stability. In one embodiment, a microemulsion composition comprising a compound of formula I, a salt of a compound of formula I and less than 20% w/w water is diluted at the point of action, for example in the mouth, to the required (at least) 80% w/w water. For example, a gel or concentrated mouthwash comprising a compound of formula I, a salt of a compound of formula I and 20% w/w water can be applied to the oral cavity. As this is brushed or gargled, the increased water level will lead to the increased stability and substantivity.

The composition containing less than or equal to 20% w/w water is preferably packaged in a container such as a bottle or tube, yet more preferably together with instructions for use. A preferred embodiment is therefore a mouthwash containing a composition as described in the preceding paragraph (containing less than or equal to 20% w/w water), packaged in a bottle.

Any method may be used to create the L2/L1 microemulsion defined herein. The skilled person will realise that the exact proportions of water, the compound of formula I and a salt of a compound of formula I will vary depending on the temperature at the time of manufacture. The values herein refer to standard temperature and pressure. It is possible to agitate the components together, i.e. mix them by shaking or stirring, although this is not required to form the microemulsion of the invention.

One method of preparing an L2/L1 microemulsion comprising water and a compound of formula I and a salt of a compound of formula I comprises adding a mixture of 70-80% w/w of formula (I) and 20-30% w/w of a salt form of formula I, simultaneously or sequentially, to water, to at least 20% w/w and preferably at least 80% w/w (of the total microemulsion composition) water.

An alternative method of forming a microemulsion according to the invention is to prepare a solution comprising water and either the compound of formula I or a salt form of the compound of formula I, and then titrate in an acid or a base until the microemulsion composition described above is formed. For example, it is possible to prepare a micellar solution of a salt form of the compound of formula I and then titrate an alkaline solution, preferably a sodium hydroxide solution, until the compound of formula I and a salt of a compound of formula I are present in the proportion discussed above, preferably 80% w/w of the compound of formula I and 20% w/w of the salt of a compound of formula I.

In a preferred embodiment, a microemulsion of a compound of formula I, a salt and water is useful in the prevention or treatment of oral disease, for example plaque formation, gingivitis, periodontitis and peri-implantitis. The microemulsion is also useful for whitening teeth. The microemulsion is preferably present as, or as part of, a toothpaste, dentifrice, gel, gum or mouthwash. The microemulsion is preferably packaged in a container such as a bottle or tube, yet more preferably together with instructions for use. A preferred embodiment is therefore a mouthwash containing a microemulsion according to the invention, packaged in a bottle.

In an alternative embodiment, the microemulsion described herein can be used in any application where a compound of formula I is useful, for example in preventing biofilm formation on a surface, preferably an industrial surface such as a metal, or preventing or treating device (implant) related infections. The use of a compound of formula (I) in preventing biofilm formation is disclosed in WO-A-2006/082393 and the prevention and treatment of device-related infections is disclosed in PCT application number PCT/GB207/002963. The content of both WO-A-2006/082393 and PCT/GB2007/002963 is incorporated by reference.

The invention claimed is:

1. An L2/L1 microemulsion composition comprising water, 3-(4-propyl-heptyl)-4-(2-hydroxyethyl)morpholine, and a salt of 3-(4-propyl-heptyl)-4-(2-hydroxyethyl)morpholine,
wherein the L2/L1 microemulsion composition increases adherence of the 3-(4-propyl-heptyl)-4-(2-hydroxyethyl) morpholine to a surface of a tooth.

2. The composition according to claim 1, wherein the salt 3-(4 propyl-heptyl)-4-(2-hydroxyethyl)morpholine is the hydrochloride salt, HCl.

3. The microemulsion composition according to claim 1, wherein the microemulsion composition comprises greater than or equal to 80% w/w water and 20% or less of the combination of the 3-(4 propyl-heptyl)-4-(2-hydroxyethyl) morpholine and a salt of 3-(4-propyl-heptyl)-4-(2-hydroxyethyl)morpholine.

4. The composition according to claim 3, comprising 98.8% water.

5. The composition according to claim 1, wherein the composition is a toothpaste, dentifrice, gel, gum or mouthwash.

6. A method of preparing an L2/L1 microemulsion composition comprising water, 3-(4 propyl-heptyl)-4-(2-hydroxyethyl)morpholine and a salt of 3-(4 propyl-heptyl)-4-(2-hydroxyethyl)morpholine comprising the steps of:
(i) forming a mixture by mixing 70-80% w/w 3-(4 propyl-heptyl)-4-(2-hydroxyethyl)morpholine with 20-30% w/w of a salt of 3-(4 propyl-heptyl)-4-(2-hydroxyethyl) morpholine; and
(ii) adding water to the mixture formed by step (1), to at least 80% w/w, thereby forming an L2/L1 microemulsion,
wherein the L2/L1 microemulsion composition increases adherence of the 3-(4 propyl-heptyl)-4-(2-hydroxyethyl) morpholine to a surface of a tooth.

7. An L2/L1 microemulsion composition comprising water and a mixture of 70-80% w/w 3-(4-propyl-heptyl)-4-(2-hydroxyethyl)morpholine and 20-30% w/w of a salt of 3-(4 propyl-heptyl)-4-(2-hydroxyethyl)morpholine,
wherein the L2/L1 microemulsion composition increases adherence of 3-(4-propyl-heptyl)-4-(2-hydroxyethyl)morpholine to a surface of a tooth.

8. A composition comprising a mixture according to claim 7 and water, wherein the water is present at less than or equal to 20% w/w.

9. The composition, according to claim 8, wherein the water is present at between 16% and 20% w/w.

10. The composition, according to claim 7, wherein the salt of 3-(4 propyl-heptyl)-4-(2-hydroxyethyl)morpholine is the hydrochloride salt, HCl.

11. A container comprising:
i. an L2/L1 microemulsion composition comprising water, 3-(4-propyl-heptyl)-4-(2-hydroxyethyl)morpholine and a salt of a 3-(4 propyl-heptyl)-4-(2-hydroxyethyl)morpholine; or
ii. a composition comprising a mixture of 70-80% w/w of a compound of 3-(4-propyl-heptyl)-4-(2-hydroxyethyl) morpholine and 20-30% w/w of a salt of 3-(4 propyl-heptyl)-4-(2-hydroxyethyl)morpholine; wherein water is optionally present and, if present, the water is present at less than or equal to 20% w/w,
wherein the L2/L1 microemulsion composition increases adherence of 3-(4-propyl-heptyl)-4-(2-hydroxyethyl)morpholine to a surface of a tooth.

12. The container according to claim 11, wherein the container is a bottle.

* * * * *

UNITED STATES PATENT AND TRADEMARK OFFICE
CERTIFICATE OF CORRECTION

PATENT NO. : 9,050,338 B2  
APPLICATION NO. : 12/742407  
DATED : June 9, 2015  
INVENTOR(S) : Thomas Arnebrant Page 1 of 2

It is certified that error appears in the above-identified patent and that said Letters Patent is hereby corrected as shown below:

IN THE CLAIMS

Column 6,
Lines 1-2, Claim 2, "salt 3-(4 propyl-heptyl)" should read --salt of 3-(4-propyl-heptyl)--.

Column 6,
Line 7, Claim 3, "3-(4 propyl-heptyl)" should read --3-(4-propyl-heptyl)--.

Column 6,
Line 16, Claim 6, "3-(4 propyl-heptyl)" should read --3-(4-propyl-heptyl)--.

Column 6,
Line 17, Claim 6, "3-(4 propyl-heptyl)" should read --3-(4-propyl-heptyl)--.

Column 6,
Line 19, Claim 6, "3-(4 propyl-heptyl)" should read --3-(4-propyl-heptyl)--.

Column 6,
Line 21, Claim 6, "3-(4 propyl-heptyl)" should read --3-(4-propyl-heptyl)--.

Column 6,
Line 27, Claim 6, "3-(4 propyl-heptyl)" should read --3-(4-propyl-heptyl)--.

Column 6,
Line 42, Claim 10, "3-(4 propyl-heptyl)" should read --3-(4-propyl-heptyl)--.

Column 6,
Line 47, Claim 11, "3-(4 propyl-heptyl)" should read --3-(4-propyl-heptyl)--.

Signed and Sealed this
Tenth Day of November, 2015

Michelle K. Lee
*Director of the United States Patent and Trademark Office*

CERTIFICATE OF CORRECTION (continued)
U.S. Pat. No. 9,050,338 B2

IN THE CLAIMS

Column 6,
Line 51, Claim 11, "3-(4 propyl-heptyl)" should read --3-(4-propyl-heptyl)--.